United States Patent [19]

Honig

[11] Patent Number: 6,125,654
[45] Date of Patent: Oct. 3, 2000

[54] BULK PRODUCTION AND USAGE OF HYPERPOLARIZED $^{129}$XENON

[75] Inventor: Arnold Honig, Manlius, N.Y.

[73] Assignee: Syracuse University, Syracuse, N.Y.

[21] Appl. No.: 09/174,277

[22] Filed: Oct. 16, 1998

[51] Int. Cl.$^7$ ....................................................... F25J 3/00
[52] U.S. Cl. ................................ 62/637; 62/3.1; 62/55.5
[58] Field of Search ............................... 62/637, 629, 3.1, 62/55.5

[56] References Cited

U.S. PATENT DOCUMENTS

| | | |
|---|---|---|
| 3,273,970 | 12/1962 | Priscu et al. . |
| 4,642,206 | 2/1987 | Honig . |
| 4,724,117 | 2/1988 | Stearns et al. . |
| 4,963,344 | 10/1990 | Gries et al. . |
| 5,357,959 | 10/1994 | Fishman . |
| 5,545,396 | 8/1996 | Albert et al. . |
| 5,612,103 | 3/1997 | Driehuys et al. . |
| 5,617,860 | 4/1997 | Chupp et al. . |
| 5,626,137 | 5/1997 | Dumoulin et al. . |
| 5,642,625 | 7/1997 | Cates, Jr. et al. ........................ 62/55.5 |
| 5,809,801 | 9/1998 | Cates, Jr. et al. ........................ 62/637 |

*Primary Examiner*—Henry Bennett
*Assistant Examiner*—Malik N. Drake
*Attorney, Agent, or Firm*—Wall Marjama Bilinski & Burr

[57] ABSTRACT

The production and usage of hyperpolarized $^{129}$Xenon which comprises providing solid xenon with either an internal (dissolved) or external (imbedded) nuclear spin relaxant, loading and positioning the solid xenon in a low temperature refrigerator operating in the range of 5 mK to 30 mK with a surrounding magnetic field of between about 10 and 20 Tesla enabling high xenon spin polarizations between about 10% and 50% to be obtained in a time of about 1–3 days owing to the properties of the relaxant, separating the xenon from the relaxant or otherwise rendering the relaxant inoperable after polarizing and thereby switching off further relaxation and insuring preservation of the polarization of the xenon in solid, liquid or gaseous form for storage or external use for long times, ranging from weeks to the order of minutes, depending on the usage conditions.

9 Claims, No Drawings

BULK PRODUCTION AND USAGE OF HYPERPOLARIZED $^{129}$XENON

BACKGROUND AND SUMMARY

The present invention relates to the production of Xenon for use in magnetic resonance imaging, and more specifically for the bulk production and usage of hyperpolarized $^{129}$Xenon.

Highly spin-polarized $^{129}$Xenon nuclei and $^3$Helium nuclei offer prospects of greatly improved medical magnetic resonance imaging (MRI) as more fully discussed in "*General Review Article : Physics Today*, June 1995, p. 17–18". It is known that the MRI contrast available with hyperpolarized $^{129}$Xenon is enhanced by 5 orders of magnitude compared with the contrast obtainable with ordinary equilibrium polarizations at room temperature, resulting in images of the lung cavity comparable to, or better than, those seen from protons in dense tissues. Furthermore, by exchanging polarization with protons in tissue or blood, the polarization of the latter can be enhanced, in some situations so as to increase greatly the sensitivity and resolution of MRI images, which could revolutionize MRI imaging techniques and open up new diagnostic applications. The exploratory medical applications thus far have been made with xenon polarized by the optical pumping technique more fully described in "Optical Pumping Method": W. Harper et al., *Phys. Rev.* A29, 3092 (1984), which can achieve suitably high polarizations, but because polarization is produced in the gaseous phase, it is costly and not very suitable for the production, storage and distribution of large quantities, which are almost certainly going to be demanded.

The general nature of the polarization methods of the present invention are related to concepts which have been developed for polarized H and D nuclei in HD molecules, for the purpose of producing polarized H and polarized D for nuclear and particle physics targets, and for other uses. U.S. Pat. No. 4,642,206 teaches these polarization processes applied to HD, but the principles rather than the particular material are the basis of the present invention and these apply to xenon and to other nuclei. In these HD and in the hyper-polarized xenon materials, a necessity is to utilize very low temperatures and high magnetic fields and spin-polarize large amounts of material in the condensed phase. The apparatus for obtaining large polarizations in high magnetic fields is cumbersome, and the main principle is to polarize under conditions wherein the relaxation times are reasonably short, for example of the order of a day, and then effect a great increase in the relaxation times so that the material can be considerably warmed, and with only a modest surrounding magnetic field, still retain for long times the polarization earlier achieved. This core concept is the "relaxation switch", manifestations of which are described in published journal articles: "HD Polarized Targets": A. Honig, Q. Fan, X Wei, A. M. Sandorfi and C. S. Whisnant, *Nuc. Instrum. and Methods* A356, 39(1995) and "HD Polarized Targets": A. Honig et al., $12^{th}$ *Intl Symposium on High Energy Spin Physics*, Amsterdam, Sep. 10–14, 1996. p. 365. *World Scientific*, 1997, and in the U.S. Pat. No. 4,642,206 patent referred to above. For the HD, one form of relaxation switch described involves introducing a concentration of $H_2$ and/or $D_2$ impurities in a metastable state in which the molecules have rotational angular momentum (ortho-$H_2$ and/or para-$D_2$). These impurities permit rapid relaxation to occur among the host HD molecules. One then waits for conversion of these impurities to a benign, rotationless state, thus shutting off the relaxation and allowing the polarization to remain for long times even at ordinary liquid helium temperatures and at modest fields less than a Tesla, in a so-called "frozen-spin" state. In this case, the "frozen-spin" occurs in a state more accessible for usage (higher T, lower B) than the state in which the polarization is originally produced (lower T, higher B). This is unlike many other frozen-spin processes, particularly those involving electron-nuclear dynamic polarization, which are discussed in the literature "$12^{th}$ *Intl. Symposium on High Energy Spin Physics*, Amsterdam, Sep. 10–14, 1996. p. 365. *World Scientific*, 1997", where the usage temperature is often lower than that used in the polarization process. This relaxation switch process is the basis of large polarized nuclear HD targets which are now in the process of being prepared for usage in nuclear physics laboratories and national accelerator sites, i.e., "LEGS Project at Brookhaven National Laboratory, Upton, N.Y.; GRAAL Project at Grenoble, France". The polarized D in HD also has application to nuclear fusion fuels, as do polarized tritium nuclei and $^3$He nuclei, for which polarization techniques have been put forward. Another relaxation switch proposed for the HD in the aforementioned U.S. Pat. No. 4,642,206 patent involves introduction of radicals by irradiation or other means, which catalyze the relaxation at the polarizing conditions of very low temperature and high magnetic field. The relaxation switch-off is then achieved by inducing recombination by waiting or annealing at higher temperatures, or by quick conversion to a liquid phase, carried out in a time sufficiently short so that the polarization doesn't decay before refreezing is effected. Other relaxation switches conceived of for the 'hydrogens' molecules include turning off the relaxation due to impurities by effecting a change of phase, such as in $D_2$, where the relaxation time in the liquid phase exceeds that in the solid phase near the melting region.

It is therefore an object of this invention to provide methods of polarizing solid xenon which can result in large quantities of the hyper-polarized xenon at a lower cost and in a more favorable form than that envisaged by the conventional optical pumping method.

The present invention is directed towards a polarization process for producing bulk hyper-polarized solid $^{129}$Xenon in a fairly short time (less than 3 days), and several relaxation switches particularly relevant to spin-polarized $^{129}$Xe, allowing its use for enhanced magnetic resonance imaging (MRI) for medical and biological research applications, and for other applications as well in the gaseous phase and "frozen-spin" configuration. We also describe several configurations of the apparatus for polarizing and utilizing hyper-polarized $^{129}$Xenon.

DETAILED DESCRIPTION OF THE INVENTION $^{129}$Xenon is a gas at room temperature. The nucleus has a spin quantum number of ½, and a moderately large nuclear magnetic moment of −0.7726 nuclear magnetons. It can be taken up into the lungs, and absorbed into blood or tissue. It has been recognized that it has potential to be imaged in the body via Magnetic Resonance Imaging techniques as described more fully in "General Review Article : *Physics Today*, June 1995, p. 17–18". However, since the gas phase is approximately 1000 times less dense (in moles/liter) than the condensed phase of tissue, its Nuclear Magnetic Resonance (NMR) signal is much weaker than that of the protons in the condensed biological material. To surmount this, hyper-polarized $^{129}$Xenon has been prepared using an optical pumping technique (Optical Pumping Method": W. Harper et al., *Phys. Rev.* A29, 3092 (1984)). In this case, the nuclear magnetization, upon which the magnetic resonance imaging sensitivity depends, can be increased by 5 orders of magnitude, making the contrast available with the $^{129}$Xenon even in the gas phase larger than that from the protons in their equilibrium room temperature condensed phases. Because the spin is ½, the retention time of the non-equilibrium highly polarized state of the hyper-polarized $^{129}$Xenon, frequently referred to as the spin-lattice relaxation time, $T_1$, is long enough even at body temperature for the $^{129}$Xenon to persist in the hyper-polarized state for sufficient time to obtain enhanced images.

As described above, the production rate of hyper-polarized 129Xenon is relatively low using optical pumping laser techniques, because the polarization is achieved in the low density gaseous phase. The present invention is directed to methods to produce high polarization in bulk solid xenon, where large quantities can be obtained relatively inexpensively. Furthermore, relaxation switches are introduced which allow the solid polarized material to be warmed up and stored under modest temperature and magnetic field conditions, and finally to be used in the gaseous phase, or dissolved in liquids while still retaining the high polarizations.

The equilibrium polarization of the weakly interacting $^{129}$Xenon nuclei in the condensed solid is given by the Brillouin function, where for a spin ½ nucleus, the polarization P is the following function of B/T, with B the applied magnetic field, T the Kelvin temperature, and k the Boltzmann constant:

$$P = \tan h[\mu(^{129}\text{Xe})B/kT]$$

Substituting the values of typical temperatures and magnetic fields used in room temperature MRI, namely about 2 Tesla and 300 K, one finds the normal $^{129}$Xe equilibrium polarization equal to about $1.9 \times 10^{-6}$. This is smaller than that of the proton, whose $\mu(^1H)$ is equal to 2.79 nuclear magnetons, resulting in a P at 2 Tesla and 300 K of $6.7 \times 10^{-6}$.

When $^{129}$Xenon is cooled down to a temperature of 10 mK, and subjected to an applied magnetic field of about 17 Tesla, both of which are commonly available in modern instrumentation, the equilibrium polarization is equal to 0.45. This more than 5 order of magnitude increase is of great importance, since the sensitivity, and hence detectability and resolution of MRI with these nuclei is proportional to the polarization. By cooling to 5 mK, a feasible prospect, the equilibrium polarization reaches 0.75.

A problem with this method is that even though these polarizations are excellent, the time to achieve them may be enormous, making the method impractical for commercial use. This is because the time to achieve polarization, called the spin-lattice relaxation time $T_1$, is inherently extremely long at low temperatures (milliKelvin) and high magnetic fields (~10 Tesla) for spin ½ nuclei, which are ordinarily relatively isolated from a thermal reservoir necessary for relaxation. The first requirement of a relaxation switch is to provide for decreasing this relaxation time. The second requirement is for the relaxant to be removable. The following relaxation switches have been found to be useful in carrying out the present invention.

A. Doping Xenon with Paramagnetic Oxygen Molecules:

Oxygen ($O_2$) is a Paramagnetic molecule which is partly soluble in liquid and solid Xenon. The large electronic magnetic dipole moment couples strongly to the nucleus and can greatly decrease the relaxation time, as has been shown in a large number of experiments since the inception of the NMR technique. A problem is that at the mK temperatures and high magnetic fields, the "motion" of the electronic spins, which is necessary for relaxation, is very small. It was also not known if the solubilities of oxygen in liquid and solid xenon are sufficient to achieve the range of relaxation times needed. We have conducted experiments with various concentrations of oxygen doped xenon, and determined the oxygen concentration, magnetic field and temperature dependencies of the $T_{1\ of}$ $^{129}$Xenon, [$T_1$($^{129}$Xenon)]. We also introduced high pressure (8 atmospheres) oxygen to liquid xenon, and utilized appropriate diffusion times (~1 hour) for the oxygen gas to enter into the liquid xenon, and subsequent suitable freeze rates (~10 K/min) of the xenon so that the oxygen is mostly retained. High polarizations greater than 10% were achieved in less than three days at oxygen molar concentrations of about 4%. This already constitutes an effective and economically utilizable situation. It is nevertheless easily improvable by increasing pressure, and varying sample configurations and diffusion times prior to freezing the liquid xenon. A strong concentration dependence was found, as well as an approximately quadratic dependence on magnetic field at high fields. A temperature dependence stronger than linear was obtained in some cases, dependent on how the material was prepared. These dependencies, especially the magnetic field one, can be associated with a degree of freedom called electron "wobble" see "Electronic Spin Wobble at High Electronic Polarization: J. S. Waugh and C. P. Slichter, *Phys. Rev.* B37, 4337 (1988)", which can account for the satisfactory value of the observed xenon nuclear spin relaxation. Thus, one can achieve high polarizations in a reasonable time, the first requirement of the relaxation switch. The second part of this relaxation switch, in which relaxation is turned off, demands removal of the oxygen without loss of the achieved high polarization. The oxygen relaxation catalyst belongs to a class of impurity relaxants whose volatility exceeds that of xenon. For this situation, we warm up the xenon in the dilution refrigerator, which has provision for thermal isolation from the mixing chamber in a "varitemp" type mode, and pump out the oxygen from the xenon, still in the solid state, at temperatures at which its vapor pressure is very low. The region between 115 K and 150 K is a good one, since the $T_1$ of the $^{129}$Xenon is acceptably long, and the self-diffusion rate of impurities (oxygen) in the lattice rises exponentially, so that a workable operating point can be found. An alternative is to liquefy the xenon and remove the oxygen by pumping through a membrane which passes oxygen but not the larger xenon molecule. Such a partially permeable membrane may also be useful when removing oxygen from the solid matrix, especially when temperatures are employed at which the vapor pressure of the xenon is substantial. Use of ultrasonic excitation in both the liquid and solid phase can facilitate the rate of oxygen degassing. The magnetic field is maintained at high values during this process so as to insure the longest possible $T_1$'s at the higher temperatures. The "vari-temp" provision inside the dilution refrigerator is one way of obtaining quick warming without seriously disturbing the dilution refrigerator. In that way, after the oxygen is removed, one can quickly re-cool the polarized xenon and store it for long times, either in the dilution refrigerator or by removing it with a cold-transfer device as more fully described in "Cold-Retrieval: N. Alexander, J Barden, Q. Fan and A. Honig, *Rev. Sci. Instrum.* 62, 2729 (1991)" and placing it in a separate vari-temp storage cryostat with a 1 K–4 K temperature capability and a magnetic field in the neighborhood of 10 Tesla, for very long storage times prior to usage, or at liquid nitrogen temperatures, for relatively short term (~day) storage. The teachings of the "Cold Retrieval" article are incorporated herein by reference. An alternative method without the "vari-temp" complication is to collect the gases from the dilution refrigerator mixing chamber, put helium exchange gas in the inner vacuum chamber of the dilution refrigerator, and physically raise the polarized xenon samples to a position along the thermal gradient where the temperature is correct for the oxygen removal operation or for a quick cryopump operation to another cryostat, using holding fields along the path of the polarized gas. After oxygen removal, the xenon is solidified and cooled for storage at temperatures between 1 K and 77 K, depending on desired storage time. Subsequently, it is warmed in the presence of a high magnetic field, and the polarized gas collected for usage. We outline later various other possibilities for convenient handling and administering of the polarized xenon gas, such as surface flash warming and use of metered capsules. Collected polarized gas may be injected into a solution for rapid medical use.

It should be noted that $O_2$ is an effective and convenient paramagnetic gas, but other paramagnetic gases, such as NO, may be similarly usable.

B. Electronic Relaxation—Inducing Impurities from Irradiation

In this case, electron spin relaxants are introduced by irradiating the xenon with ionizing radiation. This can be effected in-situ in the dilution refrigerator with a strong radioactive source, or by provision for an energetic beam of electrons or other particles to impinge on the xenon sample. But by far the easiest way to provide an irradiated sample is to use the cold-transfer device referenced above ("Cold-Retrieval: N. Alexander, J. Barden, Q. Fan and A. Honig, *Rev. Sci. Instrum.* 62, 2729 (1991)").

C. Condensation of the Xenon into a Region with Fixed Magnetic Wires

In this case, an array of magnetic wires, or a magnetic mesh, occupies the region where the xenon is to be condensed. It resembles the above case in using proximal contact of xenon with electronically-based magnetism for relaxation toward high polarization. It also requires spin-diffusion. However, for switching off the relaxation, it is in a distinguishable class where after polarization, gasification of the xenon is itself the process for relaxant removal. This may be done by quickly heating and cryopumping to another system, such as an external storage cryostat, or to another cold chamber in the dilution refrigerator, as described in section A. As also mentioned in that section, the presence of a modest magnetic field along the gas conduit path should be assured to maintain the polarization. The magnetic array or mesh can be densely packed thin wires (about 10–25 $\mu$m diameter) of nickel, nickel-coated aluminum, or other choices of magnetic materials.

D. Dispersed Magnetized Small Particles

Another relaxation switch concept consists of the dispersal of magnetized small particles encapsulated in polymers placed in the xenon, which serve as relaxation agents much as the paramagnetic oxygen did in the first example, except that the magnetic particles contain many magnetic molecules, which can be ferromagnetically coupled so that they retain their magnetization even in a weak external magnetic field. Removal after polarization can be effected by liquefying or gasifying, with the particles settling out away from the gas either gravitationally and/or as a consequence of subjecting them to a strong inhomogeneous magnetic field. Because the particles are clustered and fairly far apart in the lattice, the relaxation involves both the interaction of the magnetic particles with near xenon neighbors, and spin diffusion which carries polarization to xenon atoms far from the magnetized particles. This can provide a tailor-made magnetic field dependence by adjustment of the particle size and its dispersal, so as to gives greater latitude to the conditions of operating the relaxation switch, both in the polarizing mode and the polarization-maintenance mode.

E. Dispersal with Stable Free Radicals

The dispersal materials in this case are stable free radicals. A good example is TEMPO as described in "Stable Free Radicals: TEMPO articles by Bunyatova and by van den Brandt et al, in *Nucl. Instrum and Methods* A356 (1995)", consisting of 2,2, 6,6, -tetra methyl-piperidine-1-oxyl, which has excellent magnetic properties and is used for electron-nuclear dynamically polarized targets for nuclear spin-physics experiments. The above publication is incorporated herein by reference. If these are clustered so as to have a sufficiently large magnetic moment, for example about 10 Bohr magnetons, they can be separated in the liquid phase of the xenon by a very strong B(dB/dz) field. Former work of ours and of others with levitated diamagnetic molecules has shown that values of the product of field and field gradient up to $5\times10^{19}$ G$^2$/cm, more than enough to enough to effect the separation in the liquid, are feasible. After the separation, the usual gasification, as in D above, would follow.

F. Doping with Molecules which can be Photo-Dissociated in Solution

This form of relaxation switch method involves dissolving into liquid and solid xenon HI, HBr or other photosensitive molecules with respect to HI doping, or described in "Miyazaki, T, Tsuruta, H. and Fueki, K. J. *Phys. Chem* 87, 1611 (1983)", which is incorporated herein by reference.

G. Doping Xenon with Mixtures of o-H$_2$ and HD

This method uses doping of xenon with mixtures of o-H$_2$ and HD, in which polarization is transferred cyclically from H to $^{129}$Xe by radio-frequency induced forbidden transition adiabatic fast passage (AFP) techniques previously used to polarize D, and described in "Enhanced Nuclear Polarization of D in HD", A. Honig and H. Mano, *Phys. Rev.*, B14, 1858 (1976), which is incorporated herein by reference.

H. Electron-Nuclear Dynamic Polarization with Removable Radicals

Here, radicals such as in sections B, E, or F are introduced, but rather than serving as direct nuclear relaxation agents for polarization in very high fields and low temperatures, polarization is achieved through the electron-nuclear dynamic polarization method, in which the electron paramagnets are coupled to the nuclear paramagnets using microwave and radio-frequency excitations. These methods produce high polarization at lower fields and higher temperatures than in the nuclear equilibrium method, but require special relaxation conditions, homogeneous fields and the relaxant may be more difficult to remove. Nevertheless, they constitute a possible relaxation switch operational mode.

The following example illustrates a method for making highly polarized $^{129}$Xenon in conjunction with the use of a number of novel relaxation switches.

EXAMPLE

A large conventional top-loading dilution-refrigerator and magnet system for producing a solid polarized Xenon sample of the present invention utilizes a magnet having a bore of 80 mm. A 65 mm diameter cold finger chamber of 30 cm length is contained within the magnet bore and has a volume of about 1 liter. The $^{129}$Xenon, with incorporated paramagnetic impurities, such as oxygen, is frozen, and then cooled down to a temperature of about 10 mK in an applied magnetic field of about 15 Tesla. Condensed xenon in that volume provides about 550 usable medical "doses" of 1 hyper-polarized gaseous liter each, on a single polarization production run which typically can require between 1 to 3 days.

A solid polarized xenon sample can be cold-transferred (1 K–4 K) out of the dilution refrigerator with the Cold-Transfer Device, after which relaxation catalysts are removed in the manner described herein but from a separate storage cryostat operating at ordinary liquid helium temperatures between 1.5 and 4 K, and equipped with high (>10 Tesla) magnetic fields. This obviates need for vari-temp capability in the dilution refrigerator.

If the dilution refrigerator has a Vari-Temp feature, a thermal disconnect from the mixing chamber can be effected and the sample can be warmed quickly. Then the gas can be cryopumped directly into another cryostat, as long as a retaining field along the pumped path is activated to retain the polarization. The polarized xenon adiabatically follows the guide field.

The cryopumping described above can be into capsules with a small hole for entry and exit of the gas. The volume of the capsule would correspond to that needed for a medical usage dose, for example 2 cm$^3$, corresponding to about 1 liter when gasified. Then, individual polarized gas doses can be retrieved.

The original condensation of xenon can be into capsules with holes, and retrieved with a cold-retrieval device, or separately retrieved as needed from a storage cryostat. The capsules can be on a circular turret, with sequential injection and retrieval using a reusable seal, such as an indium lined cone pair. Methods A,B, F, and H are easily adaptable to this type of production arrangement, but the others can be accommodated by variations of the turret idea as well.

Liquefying and gasifying the solid xenon can be done by direct contact heating, strong infra-red radiative heating, inductive heating from imbedded conductors, or by flash surface heating. The latter could provide a way of obtaining small, approximately measured doses from a bulk polarized solid sample, without using metered capsules.

In one embodiment electron spin, relaxants are introduced by irradiating the xenon with ionizing radiation. This is accomplished in-situ in the dilution refrigerator with a strong radioactive source, or by provision for an energetic beam of electrons or other particles to impinge on the xenon sample. A preferred way to provide an irradiated sample is to use the cold-transfer device. This device is placed near an X'ray or other source of ionizing radiation with the sample at temperatures between about 1 and 4 K. After the radicals are formed, they persist at the low temperatures. The sample is then transferred into a dilution refrigerator which has a central access from the top, engaged to the mixing chamber, and then disengaged from the cold-transfer device which is then removed. The sample can now be polarized by the usual way of coming to equilibrium at low (~10 mK temperature and high (15–20 T) magnetic field. The relaxation switch is subsequently turned off by heating the sample, thereby annealing the defects. This usually occurs in the solid without a large increase of the temperature, but is certainly effected by liquefaction. This form of relaxation switch is an example of a class of relaxants in which additional impurities do not have to be physically extracted, as with doping with paramagnetic oxygen molecules. This presents some additional options for handling the resulting frozen-spin polarized material.

Another form of relaxation switch method involves dissolving into liquid and solid xenon HI, HBr or other photosensitive molecules. The material, crystallized in a reasonably transparent state, is then irradiated with ultra-violet (and in some cases visible) light, causing radicals to form, which then catalyze the relaxation. After polarization is completed, the photo-induced radicals are eliminated. This acts much as the irradiation with high energy particles proposed for the HD as well as for xenon in the embodiment described above, except it can be turned on by light (UV or visible), and off, by recombination occurring spontaneously in the absence of light, or by infrared light stimulation or annealing heating.

In a further embodiment, radicals such as those described above are introduced, but rather than serving as direct nuclear relaxation agents for polarization in very high fields and low temperatures, polarization is achieved through the electron-nuclear dynamic polarization method, in which the electron paramagnets are coupled to the nuclear paramagnets using microwave and radio-frequency excitations. These methods produce high polarization at lower fields and higher temperatures than in the nuclear equilibrium method, but require special relaxation conditions, homogeneous fields and the radicals are more difficult to remove. Nevertheless, it is a possible relaxation switch method. After polarization, the microwave frequency employed is turned off and the electronic paramagnets removed as before. There are combinations of this technique with our other methods described above for implementing the relaxation switch, which is at the heart of the frozen-spin goal.

Another embodiment uses doping of xenon with mixtures of o-$H_2$ and HD, in which polarization is transferred from H to $^{129}$Xe by forbidden transition adiabatic fast passage (AFP) techniques previously used to polarize D. As an example, a mole-fraction mixture of about $3 \times 10^{-4}$ o-$H_2$, 0.2 HD and 0.8 Xenon results in a very high polarization of H in a reasonable time, and a long spin-lattice relaxation time of the H. The H polarization is transferred to the deuterons at low magnetic fields, as described in the original publication "Enhanced Nuclear Polarization of D in HD", A. Honig and H. Mano, Phys. Rev. B14, 1858 (1976)", which is incorporated herein by reference. The transfer cycle can be repeated several times for attaining maximum xenon polarization. If solubility of $H_2$ (and HD) in Xenon is large enough, the mole fraction of HD can be somewhat increased and the number of AFP polarization transfer cycles reduced. Removal of the hydrogens is not necessarily required, but one can do it if needed by techniques such as described in section A for oxygen removal.

These examples are not meant to be totally comprehensive, but rather applicable and illustrative. The broad aspect of the invention is the relaxation switch concept. Numerous embodiments have been described, but other methods not explicitly described can be considered as included within the broad scope of the invention.

We claim:

1. A method for the production and usage of hyperpolarized $^{129}$Xenon which comprises providing solid xenon with either an internal (dissolved) or external (imbedded) nuclear spin relaxant, loading and positioning the solid xenon in a low temperature refrigerator operating in the range of 5 mK to 30 mK with a surrounding magnetic field of between about 10 and 20 Tesla enabling high xenon spin polarizations between about 10% and 50% to be obtained in a time of about 1–3 days owing to the properties of the relaxant, separating the xenon from the relaxant or otherwise rendering the relaxant inoperable after polarizing and thereby switching off further relaxation and insuring preservation of the polarization of the xenon in solid, liquid or gaseous form for storage or external use for long times, ranging from weeks to the order of minutes, depending on the usage conditions.

2. A method for the bulk production and usage of hyperpolarized $^{129}$Xenon which comprises:

(a) preparing a sample of liquid xenon with a high concentration of dissolved oxygen by exposing the xenon to high pressure oxygen gas in a limited volume at suitably low liquid xenon temperatures and allowing for the oxygen gas to diffuse throughout the liquid xenon;

(b) freezing and cooling the oxygen-doped xenon down to a temperature of about 100 K at a rapid rate, with further cooling at a moderate rate down to mK temperatures in the range 5 mK to 30 mK;

(c) applying a magnetic field in the range of 10 to 20 Tesla to said oxygen doped xenon to establish an equilibrium polarization between about 10% and 50% for the temperature range of about 10 mK to 30 mK, and in a time of at most several days;

(d) initiate a relaxation switch-off after (c) above, by removing the oxygen relaxant by a combination of suitable gas separation methods selected from the group consisting of warming and simple mechanical pumping or cryopumping of the evolved gas, ultrasonic stimulation of desorption of the gas, and the use of gas-selective permeability membranes;

(e) re-cooling to liquid helium temperatures for long term storage, or to liquid nitrogen temperatures, for short term usage; and (f) gasifying the xenon for usage.

3. A method for the bulk production and usage of hyperpolarized $^{129}$Xenon which comprises:

(a) the method of claim 1 in which the relaxation agent is the result of irradiation of solid cold xenon either in-situ or in an external cold-transferable apparatus wherein after irradiation, the solid is placed in a dilution refrigerator and cooled to mK temperatures and placed in a large magnetic field, until high polarization is obtained;

(b) operate a relaxation switch-off after (a) by heating and annealing out the radiation defects or by causing recombination of the defects by other means; and (c) re-cool and gasify for usage.

4. A method for the bulk production and usage of hyperpolarized $^{129}$Xenon which comprises:

(a) the method of claim 1 in which the relaxation agent is in the form of an external matrix of paramagnets or magnets in which the solid xenon is imbedded, with the structure containing the solid xenon placed in a dilution refrigerator and cooled to mK temperatures in the presence of a surrounding large magnetic field;

(b) initiate a relaxation switch-off after (a) by gasifying and thus physically removing the xenon from the structure containing the external relaxant; and (c) re-cooling and gasifying for usage.

5. A method for the bulk production and usage of hyperpolarized $^{129}$Xenon which comprises:

(a) the method of claim 1 in which the relaxation agent is in the form of dispersed magnetic small particles, and the thus prepared solid xenon is placed in a dilution refrigerator and cooled to mK temperatures in the presence of a surrounding large magnetic field until high polarization is obtained;

(b) initiating a relaxation switch-off after (a) by gasifying and thus physically removing the xenon from the structure containing the external relaxant or by sedimenting out the particles from liquid xenon with a centrifuge or force field due to a strong magnetic field gradient; and (c) re-cool and gasify for usage.

6. A method for the bulk production and usage of hyperpolarized $^{129}$Xenon which comprises:

(a) the method of claim 1 in which the relaxation agent is in the form of dispersed or dissolved stable free radicals, placing the solid xenon in a dilution refrigerator and cooling to mK temperatures in the presence of a surrounding large magnetic field until high polarization is obtained;

(b) initiating relaxation switch-off after step (a) above by isolating the xenon from the free radicals through warming the xenon and collecting it free of the free radicals via mechanical pumping or cryopumping the xenon into another container directly or through a separating membrane, or by reacting the free radicals with a chemical agent and then collecting the xenon; and (c) re-cool and gasify for usage.

7. A method for the bulk production and usage of hyperpolarized $^{129}$Xenon which comprises:

(a) the method of claim 1 in which the relaxation agent is in the form of dissolved molecules which can be photo-dissociated by visible or ultraviolet light irradiation in the solid xenon, placing the solid xenon in a dilution refrigerator and cooling to mK temperatures in the presence of a surrounding large magnetic field, until high polarization is obtained;

(b) initiating a relaxation switch-off after step (a) above by ceasing irradiation and allowing spontaneous recombination to occur or by heating to a temperature where rapid recombination occurs among the photo-dissociation products, and separating the xenon from the photosensitive chemicals or their chemical products by mechanical pumping or cryopumping the xenon into another container directly or through a separating membrane and then collecting the xenon; and (c) re-cool and gasify for usage.

8. A method for the bulk production and usage of hyperpolarized $^{129}$Xenon which comprises:

(a) the method of claim 1 in which the relaxation agent is in the form of dissolved HD and $H_2$ gas, placing the solid xenon in a dilution refrigerator and cooling to mK temperatures in the presence of a surrounding large magnetic field and cyclically transfer polarization from the H in HD by radio-frequency methods until high polarization is obtained, (b) initiating a relaxation switch-off after step (a) above by ga; separation; and (c) re-cool and gasify for usage.

9. A method for the bulk production and usage of hyperpolarized $^{129}$Xenon which comprises:

(a) the method of claim 1 in which the relaxation agent is in the form of at least one of the group consisting of dissolved paramagnetic material such as the $O_2$, irradiation products, the dissolved stable radicals, or dissolved photosensitive molecules, in which the solid xenon is placed in a dilution refrigerator, and cooled only to about 50 to 500 mK and placed in a homogeneous magnetic field of a few Tesla, with the polarization of the xenon being attained by microwave irradiation and electron-nuclear dynamic polarization;

(b) initiating a relaxation switch-off after step (a) above; and (c) re-cool and gasify for usage.

* * * * *